(12) United States Patent
Chang

(10) Patent No.: US 10,603,457 B2
(45) Date of Patent: Mar. 31, 2020

(54) RESPIRATORY MASK

(71) Applicant: Hsiner Co., Ltd., Taichung (TW)

(72) Inventor: Eric Chang, Taichung (TW)

(73) Assignee: HSINER CO., LTD., Taichung (TW)

( * ) Notice: Subject to any disclaimer, the term of this patent is extended or adjusted under 35 U.S.C. 154(b) by 286 days.

(21) Appl. No.: 15/681,719

(22) Filed: Aug. 21, 2017

(65) Prior Publication Data

US 2018/0304035 A1    Oct. 25, 2018

(30) Foreign Application Priority Data

Apr. 20, 2017   (TW) .............................. 106113277 A

(51) Int. Cl.
*A61M 16/06* (2006.01)

(52) U.S. Cl.
CPC .... *A61M 16/0622* (2014.02); *A61M 16/0616* (2014.02); *A61M 16/0683* (2013.01)

(58) Field of Classification Search
CPC .............. A61M 16/0683; A61M 16/06; A61M 16/0616; A61M 16/0622; A61M 16/0816; A61M 16/0633; A61M 16/0825; A61M 16/0611; A61M 16/08; A61M 16/0638; A61M 16/0666; A61M 16/0875; A61M 2210/0618; A61M 16/0644; A61M 16/0057; A61M 16/065; A61M 16/0655; A61M 2016/0027; A61M 2205/42; A61M 16/0858; A61M 2016/0661; A61M 16/0605; A61M 16/16; A61M 16/0003; A61M 16/0066; A61M 16/0069; A61M 16/024; A61M 16/1045; A61M 2016/0039; A61M 2202/0208; A61M 2205/0216; A61M 2205/3331; A61M 2205/3368; A61M 2230/432; A61M 15/009; A61M 16/0051; A61M 16/022; A61M 16/0415; A61M 16/0463; A61M 16/0493; A61M 16/0672; A61M 16/0833; A61M 16/085; A61M 16/1065; A61M 16/107; A61M 16/109; A61M 16/125; A61M 16/205; A61M 16/208; A61M 16/209; A61M 16/22; A61M 2205/02; A61M 2205/0244; A61M 2205/14; A61M 2205/332; A61M 2205/3327; A61M 2205/50;

(Continued)

(56) References Cited

U.S. PATENT DOCUMENTS 8,336,547 B1 *  12/2012  Ritchie ................ A62B 18/025
                                                128/200.24
2009/0101147 A1 *  4/2009  Landis ............... A61M 16/0666
                                                128/204.18

(Continued)

*Primary Examiner* — Kendra D Carter
*Assistant Examiner* — Paige Kathleen Bugg
(74) *Attorney, Agent, or Firm* — Hamre, Schumann, Mueller & Larson, P.C.

(57) ABSTRACT

A respiratory mask includes a mask frame and a soft mask pad. The mask frame includes a ring-shaped base which is disposed at the front end of the mask pad, and a pair of wing portions which are connected to two opposite sides of the ring-shaped base and each of which is formed with a free end face. The mask pad includes an abutting portion, and is transformable between a non-sealing state, where the abutting portion is separated from the free end faces, and a sealing state, where the abutting portion abuts against the free end faces.

5 Claims, 8 Drawing Sheets

(58) Field of Classification Search
CPC .... A61M 2205/583; A61M 2205/6045; A61M 2206/14; A61M 2207/00; A61M 2209/06; A61M 2209/088; A61M 2230/04; A61M 2230/202; A61M 2230/205; A61M 2230/435; A61M 2230/50
See application file for complete search history.

(56) References Cited

U.S. PATENT DOCUMENTS

2010/0319700 A1\* 12/2010 Ng ........................ A61M 16/06
128/206.28
2017/0119989 A1\* 5/2017 White ............... A61M 16/0666

\* cited by examiner

RESPIRATORY MASK

CROSS-REFERENCE TO RELATED APPLICATION

This application claims priority of Taiwanese Application No. 106113277, filed on Apr. 20, 2017.

FIELD

The disclosure relates to a type of medical equipment, more particularly a respiratory mask that assists in breathing.

BACKGROUND

There exists a type of respiratory mask, one referred in US patent application publication No. US 2017/0021123 A1, which includes a support frame, a mask pad, and an air duct. The support frame includes a ring-shaped base portion, an insert portion, a positioning pin, and two wing portions. The insert portion extends rearwardly from an inner edge of the base portion, and defines an air channel. The positioning pin extends rearwardly from a top end of the base portion, and has a hooked end distal from the base portion. The wing portions are respectively disposed at lateral sides of the base portion. The mask pad has a main body, a through hole, and a face pad. The main body has an open end portion abutting separably against the base portion of the support frame and defining an opening for extension of the insert portion of the support frame thereinto, and is clamped separably between the wing portions of the support frame. The through hole is formed in the main body. The positioning pin of the support frame engages removably the through hole such that the main body is fastened releasably on the support frame by the positioning pin and the wing portions. The face pad is mounted on the main body for contacting a face of a user. The air duct is connected to the support frame and communicates with the air channel.

While this prior art allows easy assembling and disassembling between the support frame and the mask pad, the respiratory mask can easily deform, which in turn causes leakage or the air from the air duct.

SUMMARY

Therefore, an object of the disclosure is to provide a respiratory mask that can alleviate at least one of the drawbacks of the prior art.

According to the disclosure, the respiratory mask includes a mask frame and a soft mask pad that has a rear end configured to contact a patient's face and a front end opposite to the rear end.

The mask frame includes a ring-shaped base disposed at the front end of the mask pad, and a pair of wing portions. The ring-shaped base has an inner periphery, an outer periphery surrounding the inner periphery, and a tubular insert portion protruding rearwardly from the inner periphery to extend into the mask pad. The wing portions are connected to the outer periphery at two opposite sides of the ring-shaped base, and project rearwardly to respectively extend over two opposite sides of the mask pad. Each of the wing portions includes a connecting segment connected to and extending rearwardly from the outer periphery of the ring-shaped base, and a support segment connected to and extending rearwardly and upwardly from the connecting segment, with the support segment being formed with a free end face that has a positioning notch indented from the free end face.

The mask pad includes a front wall that abuts against a rear side of the ring-shaped base and has an inner peripheral edge defining an opening for extension of the tubular insert portion of the ring-shaped base, a sleeve portion extending rearwardly from the inner peripheral edge of the front wall and sleeving around the tubular insert portion of the ring-shaped base, a surrounding wall portion rearwardly extending from an outer periphery of the front wall around the sleeve portion, a pair of protrusions protruding oppositely from the surrounding wall portion for respectively engaging the positioning notches of the wing portions, a facial sealing pad portion disposed rearwardly of the surrounding wall portion and opposite to the front wall, and an abutting portion obliquely extending from the surrounding wall portion to the facial sealing pad portion and having two outer surface regions that respectively face the wing portions and that diverge outwardly from the surrounding wall portion to the facial sealing pad portion. Each of the outer surface regions has a first site proximate to a corresponding one of the protrusions, and a second site spaced angularly from and located above the first site. Each of the outer surface regions of the abutting port on forms an included angle with respect to a line parallel to an axis of the tubular insert portion and the sleeve portion. The included angle gradually increases from the first site to the second site. The wing portions extend over an outer surface of the surrounding wall portion. The mask pad is transformable between a non-sealing state, where the outer surface regions of the abutting portion are separated from the free end faces of the wing portions, and a sealing state, where the outer surface regions of the abutting portion respectively abut against the free end faces of the wing portions.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
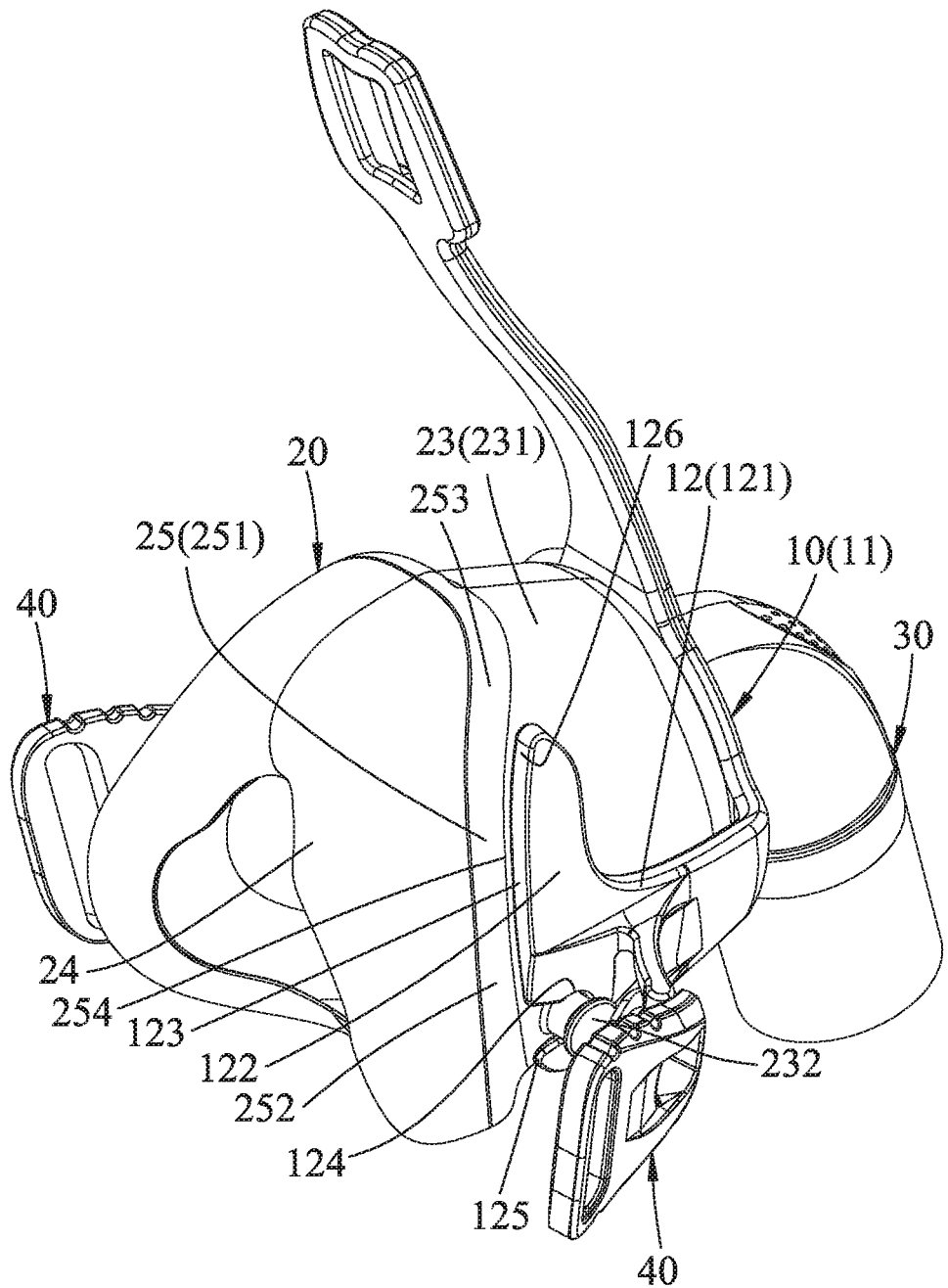
FIG. 1 is an assembled perspective view of an embodiment of a respiratory mask according to the disclosure.
Figure 2:
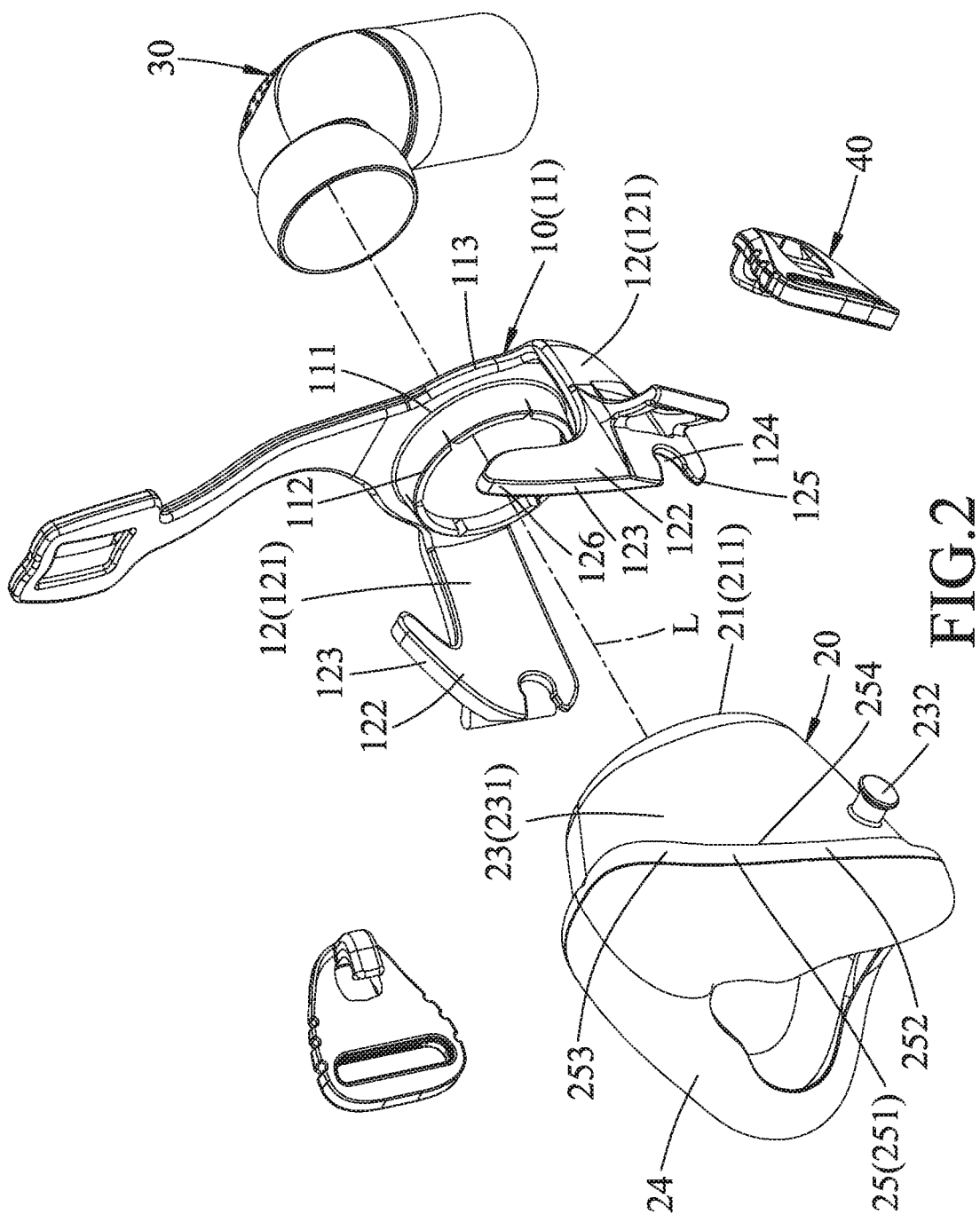
FIG. 2 is an exploded perspective view of the embodiment.

Referring to FIGS. 1 to 2, an embodiment of a respiratory mask according to the disclosure includes a mask frame 10 and a soft mask pad 20 that has a rear end configured to contact a patient's face and a front end opposite to the rear end. In addition, the mask frame 10 can be provided with an air duct 30 and a pair of strap-connecting members 40, which are not the essential feature of the disclosure and can be selected by a person skilled in the art, and thus, the detailed description thereof is omitted herein.

The mask frame 10 is made of a rigid plastic material, and includes a ring-shaped base 11, and a pair of wing portions 12 which are respectively connected at two opposite sides of the ring-shaped base 11. The ring-shaped base 11 is disposed at the front end of the mask pad 20, and has an inner periphery 111, an outer periphery 113 surrounding the inner periphery 111, and a tubular insert portion 112 protruding rearwardly from the inner periphery 111 to extend into the mask pad 20. The two wing portions 12 are connected to the outer periphery 113 at the opposite sides of the ring-shaped base 11 and project rearwardly to respectively extend over two opposite sides of the mask pad 20. Each of the wing portions 12 includes a connecting segment 121 connected to and extending rearwardly from the outer periphery 113 of the ring-shaped base 11, and a support segment 122 connected transversely to and extending rearwardly and upwardly from the connecting, segment 121 and thus forming an L-shape with the connecting segment 121. The support segment 122 is formed with a free end face 123 that has a positioning notch 124 indented from the free end face 123, which is convexed and has a lower end 125 proximate to the positioning notch 124, and an upper end 126 higher than the lower end 125. The free end face 123 extends curvedly from the lower end 125 to the upper end 126, and the upper end 126 is inclined in a direction toward the ring-shaped base 11.

The mask pad 20 is made of a silicone material that can undergo flexural deformation to bear a cup-like shape, and is installed on the mask frame 10. Further referring to FIG. 3, the mask pad 20 includes a front wall 21, a sleeve portion 22, a surrounding wall portion 23, a facial sealing pad portion 24 and an abutting portion 25. The front wall 21 has a bottom surface 211 sealingly abuts against a rear surface of the ring-shaped base 11, and an inner peripheral edge defining an opening for extension of the tubular insert portion 112 of the ring-shaped base 11. The sleeve portion 22 extends rearwardly from the inner peripheral edge of the front wall 21 and sleeves around the tubular insert portion 112 of the ring-shaped base 11. The surrounding wall portion 23 rearwardly extends from an outer periphery of the front wall 21 around the sleeve portion 22, and has an outer surface 231 over which the wing portions 12 extend, and a pair of protrusions 232 protruding oppositely from the outer surface 231 for respectively engaging the positioning notches 124. The facial sealing pad portion 24 is disposed rearwardly of the surrounding wall portion 23 and opposite to the front wall 21, and has a thickness less than that of the surrounding wall portion 23. The abutting portion 25 obliquely extends from the surrounding wall portion 23 to the facial sealing pad portion 24, and has a thickness that gradually decreases from the surrounding wall portion 23 to the sealing pad portion 24. The abutting portion 25 has two outer surface regions 251 that respectively face the wing portions 12 and that diverge outwardly from the surrounding wall portion 23 to the facial sealing pad portion 24. Each of the outer surface regions 251 has a curvature matchable with that of the free end face 123 of the support segment 122 of the corresponding wind portion 12.

Figure 5:
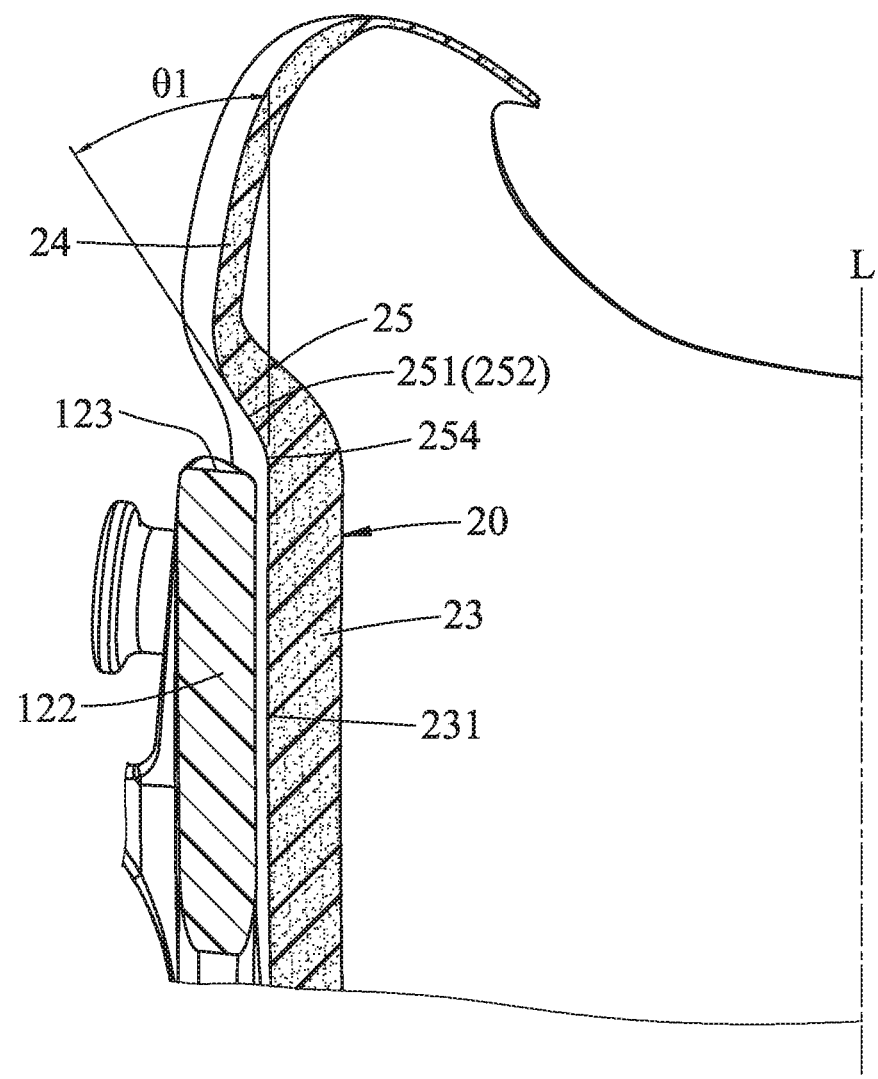
FIG. 5 is a fragmentary sectional view taken along line V-V in FIG. 4.
Figure 6:
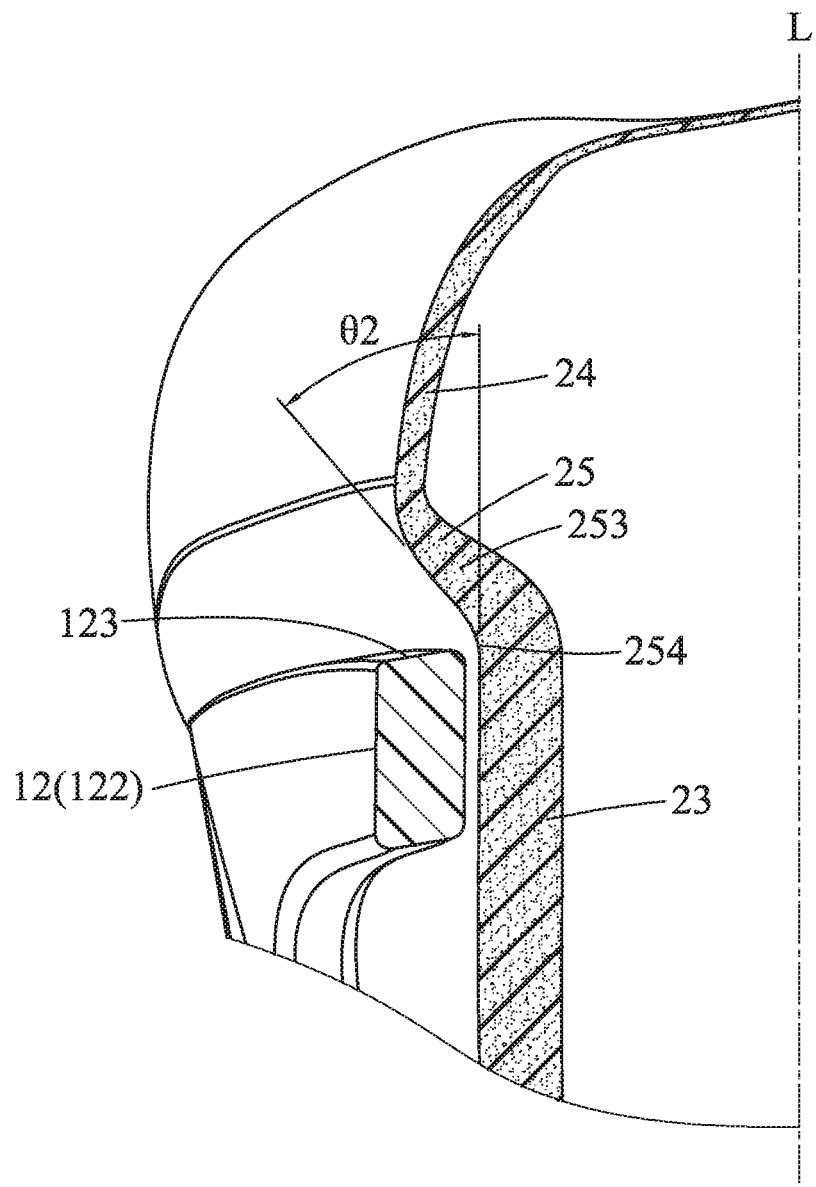
FIG. 6 is a fragmentary sectional view taken along line VI-VI in FIG. 4.

Each of the outer surface regions 251 has a first site 252 proximate to a corresponding one of the protrusions 232, a second site 253 spaced angularly from and located above the first site 252, and a bordering end 254 adjoining the surrounding wall portion 23, and forms an included angle with respect to a line parallel to an axis (L) of the tubular insert portion 112 and the sleeve portion 22. The included angle gradually increases from the first site 252 to the second site 253. Referring to FIGS. 5 and 6, a first angle $\theta 1$ formed between the first site 252 and the line parallel to the axis (L) is smaller than a second angle $\theta 2$ formed between the second site 253 and the line parallel to the axis (L).

The mask pad 20 is transformable between a non-sealing state and a sealing state. As shown in FIGS. 3 through 6, after the embodiment of the respiratory mask is fully assembled, the facial sealing pad portion 24 can be placed outside the nose portion of a user without any deformation. Before transfer of pressurized air into the respiratory mask through the air duct 30, the mask pad 20 is in the non-sealing state, in which the outer surface regions 251 of the abutting portion 25 are separated from the free end faces 123 of the wing portions 12 (i.e., having no physical contact with the free end faces 123), and the bordering end 254 is spaced apart from the free end face 123 of a corresponding one of the wing portions 12 with an interval of not less than 2 mm in this embodiment.

Figure 3:
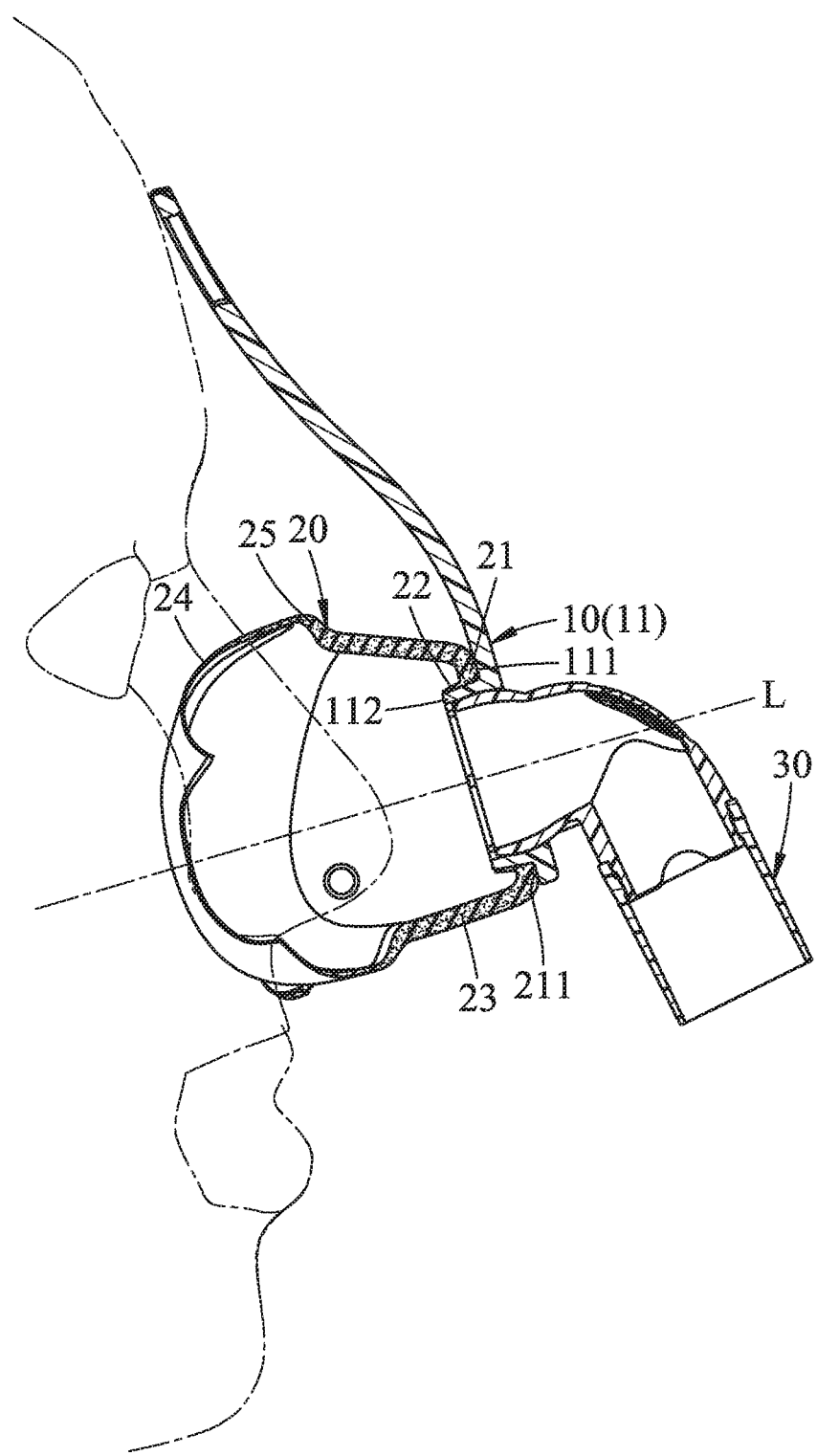
FIG. 3 is an assembled sectional view of the embodiment.
Figure 4:
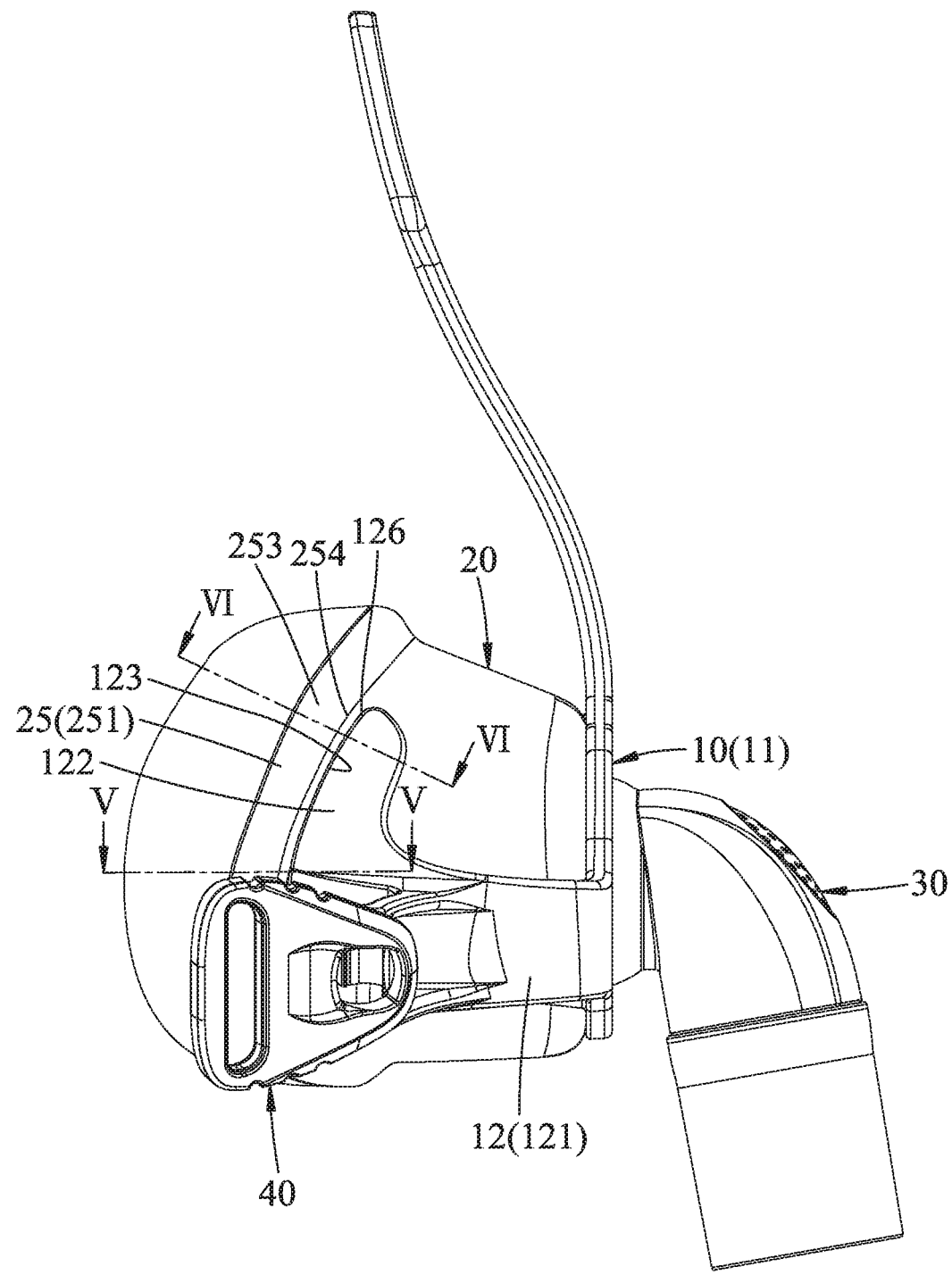
FIG. 4 is an assembled side view of the embodiment.
Figure 7:
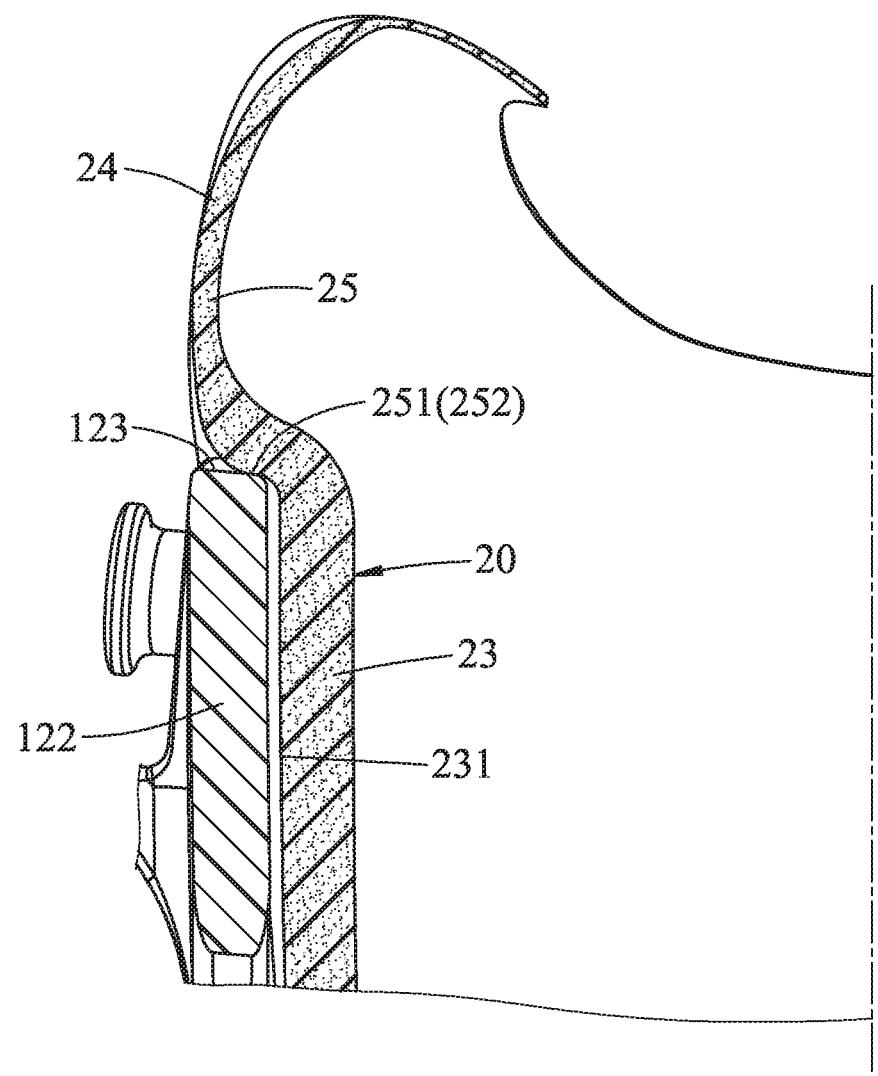
FIG. 7 is a similar view as FIG. 5, but illustrating the embodiment in an inflated form.
Figure 8:
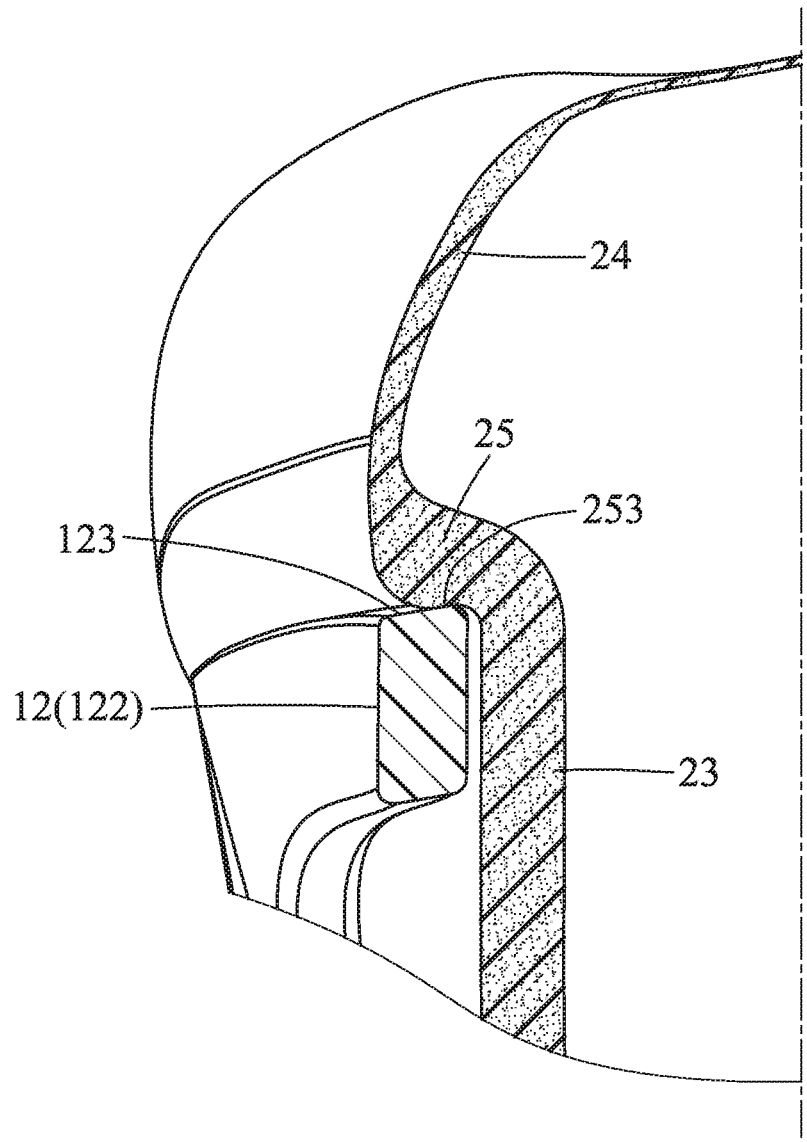
FIG. 8 is a similar view as FIG. 6, but illustrating the embodiment in the inflated form.

Referring to FIGS. 3, 7 and 8, when the air duct 30 transfers the pressurized air into the interior of the mask pad 20, the pressure inside the mask pad 20 would become greater than atmospheric pressure, causing the bottom surface 211 of the front wall 21 to tightly fit onto the inner periphery 111, and with the sleeve portion 22 sleeving around the tubular insert portion 112 of the ring-shaped base 11. The pressurized air would be trapped and prevented from escaping through a contact portion between the mask pad 20 and the ring-shaped base 11, thereby trans forming the mask pad 20 into the sealing state. At the same time, the pressurized air would cause the surrounding wall portion 23, the facial sealing pad portion 24 and the abutting portion 25 to inflate, especially the outer surface regions 251 of the abutting portion 25, which would respectively abut against the free end faces 123 of the wing portions 12.

At this time, with the abutting portion 25 abutting onto the free end faces 123 of the wing portions 12, the mask pad 20, besides being able to remain stably mounted onto the user's face, would develop a buffer effect against deformation caused by the pressurized air, thereby ensuring quality air delivery to the user. Also, given that the bordering end 254 is originally spaced apart from the free end face 123 of a corresponding one of the wing portions 12 with an interval of not less than 2 mm, the abutting portion 25 would have more flexibility in deformation. In addition, given that the first angle $\theta 1$ formed between the first site 252 and the line parallel to the axis (L) is smaller than the second angle $\theta 2$ formed between the second site 253 and the line parallel to the axis (L), the deformation capability of the abutting portion 25 corresponding to the second site 253 is better than the one corresponding to the first site 252, thereby ensuring that the facial sealing pad portion 24 is securely fastened to the nose bridge of the user.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A respiratory mask, comprising:
   a soft mask pad having a rear end configured to contact a patient's face and a front end opposite to said rear end; and
   a mask frame including
      a ring-shaped base disposed at said front end of said mask pad and having an inner periphery, an outer periphery surrounding said inner periphery, and a tubular insert portion protruding rearwardly from said inner periphery to extend into said mask pad, and
      a pair of wing portions, which are connected to said outer periphery at two opposite sides of said ring-shaped base and which project rearwardly to respectively extend over two opposite sides of said mask pad, each of said wing portions including a connecting segment connected to and extending rearwardly from said outer periphery of said ring-shaped base, and a support segment connected to and extending rearwardly and upwardly from said connecting segment, said support segment being formed with a free end face that has a positioning notch indented from said free end face;
   said mask pad including
      a front wall that abuts against a rear side of said ring-shaped base and has an inner peripheral edge defining an opening for extension of said tubular insert portion of said ring-shaped base,
      a sleeve portion extending rearwardly from said inner peripheral edge of said front wall and sleeving around said tubular insert portion of said ring-shaped base,
      a surrounding wall portion rearwardly extending from an outer periphery of said front wall around said sleeve portion,
      a pair of protrusions protruding oppositely from said surrounding wall portion for respectively engaging said positioning notches of said wing portions,
      a facial sealing pad portion disposed rearwardly of said surrounding wall portion and opposite to said front wall, and
      an abutting portion obliquely extending from said surrounding wall portion to said facial sealing pad portion and having two outer surface regions that respectively face said wing portions and that diverge outwardly from said surrounding wall portion to said facial sealing pad portion, each of said outer surface regions having a first site proximate to a corresponding one of said protrusions, and a second site spaced angularly from and located above said first site,
   wherein each of said outer surface regions of said abutting portion forms an included angle with respect to a line parallel to an axis (L) of said tubular insert portion and said sleeve portion, the included angle gradually increasing from said first site to said second site,
   wherein said wing portions extend over an outer surface of said surrounding wall portion, said mask pad is transformable between a non-sealing state, where said outer surface regions of said abutting portion are separated from said free end faces of said wing portions, and a sealing state, where said outer surface regions of said abutting portion respectively abut against said free end faces of said wing portions, and
   wherein each of said outer surface regions of said abutting portion further includes a bordering end adjoining said surrounding wall portion, said bordering end is spaced apart from said free end face of a corresponding one of said wing portions with an interval of not less than 2 mm when said mask pad is in the non-sealing state.

2. The respiratory mask of claim 1, wherein said support segment is connected transversely to said connecting segment and forms an L-shape with said connecting segment.

3. The respiratory mask of claim 1, wherein said facial sealing pad portion has a thickness less than that of said surrounding wall portion, said abutting portion having a thickness that gradually decreases from said surrounding wall portion to said facial sealing pad portion.

4. The respiratory mask of claim 1, wherein said free end face of each of said wing portions is convexed and has a lower end proximate to said positioning notch and an upper end higher than said lower end, said free end face extending curvedly from said lower end to said upper end, said upper end being inclined in a direction toward said ring-shaped base.

5. The respiratory mask of claim 4, wherein each of said outer surface regions of said abutting portions has a curvature matchable with that of said free end face of one of said wing portions.

* * * * *